United States Patent [19]
Krivoshlykov et al.

[11] Patent Number: 5,557,701
[45] Date of Patent: Sep. 17, 1996

[54] POWER LASER DELIVERY FIBER SYSTEM WITH ENHANCED DAMAGE THRESHOLD

[75] Inventors: Sergej G. Krivoshlykov, Moscow, Russian Federation; Wolfgang Neuberger, Monchengladbach, Germany

[73] Assignee: CeramOptec Industries, Inc., East Longmeadow, Mass.

[21] Appl. No.: 339,502

[22] Filed: Nov. 14, 1994

Related U.S. Application Data

[63] Continuation-in-part of Ser. No. 161,327, Dec. 2, 1993, Pat. No. 5,370,643.

[51] Int. Cl.$^6$ .............................. G02B 6/02; G03H 1/00
[52] U.S. Cl. .................. 385/124; 385/31; 385/38; 385/123; 359/1; 359/15; 359/19; 359/34
[58] Field of Search .................................. 385/123, 124, 385/116, 15, 27, 28, 31, 38; 359/1, 15, 19, 27, 32, 34

[56] References Cited

U.S. PATENT DOCUMENTS

| | | | |
|---|---|---|---|
| 3,658,407 | 4/1972 | Kitano et al. | 385/124 X |
| 4,053,205 | 10/1977 | Miller | 385/124 X |
| 4,421,382 | 12/1983 | Doi et al. | 385/124 X |
| 4,593,975 | 6/1986 | Nakauchi et al. | 385/124 X |
| 4,674,843 | 6/1987 | Baba et al. | 385/124 X |
| 4,693,244 | 9/1987 | Daikuzono | 128/303.1 |
| 4,971,423 | 11/1990 | Nakata et al. | 385/124 X |
| 4,997,250 | 3/1991 | Ortiz, Jr. | 385/33 X |
| 5,370,643 | 12/1994 | Krivoshlykov et al. | 606/16 |
| 5,390,274 | 2/1995 | Toyoda et al. | 385/124 |

FOREIGN PATENT DOCUMENTS

| | | | |
|---|---|---|---|
| 438653A2 | 7/1991 | Germany | G02B 6/18 |

*Primary Examiner*—Brian Healy
*Attorney, Agent, or Firm*—Bolesh J. Skutnik

[57] ABSTRACT

A flexible fiber optic delivery system for medical and industrial applications is described that can transmit high laser power densities and optical images. A parabolic-index profile of a graded-index fiber is perturbed so as to prevent strong localization of a laser beam in the fiber's recurring focal regions. This permits transmission of high laser powers without danger of fiber damage. An additional gain in carrying capacity for the system is achieved by using a wavefront perturbation system between the laser source and the graded-index fiber. Optical image transmission is achieved by using a measured perturbation to a parabolic-index profile of the graded-index fiber with a prescribed length and a wavefront reconstruction system in combination with the wavefront perturbation system. The system has an increased laser induced damage threshold and can transmit highly focused optical images.

7 Claims, 3 Drawing Sheets

POWER LASER DELIVERY FIBER SYSTEM WITH ENHANCED DAMAGE THRESHOLD

REFERENCE TO RELATED CASE

This is a continuation-in-part of U.S. patent application Ser. No. 08/161,327 filed on Dec. 2, 1993 by Wolfgang Neuberger, and Sergej G. Krivoshlykov, inventors, entitled "Multiple Effect Laser Delivery System for Medical Procedures," now U.S. Pat. No. 5,370,643.

BACKGROUND OF THE INVENTION

1. Field of the Invention

The invention relates to a power laser delivery system for medical and industrial applications and more specifically to a laser delivery system which uses a graded index fiber manufactured and utilized to transmit a high level of energy without sustaining damage.

2. Information Disclosure Statement

Power laser delivery devices are becoming increasingly more important in medicine for effectively performing procedures ranging from tissue cutting, coagulating, welding and destruction of kidney stones to ablation of arterial plaques and in industry. The medical and industrial laser delivery systems generally employ optical fibers to carry laser radiation to remote targets. They provide freedom of movement and reliability unmatched by articulated arm laser delivery systems. They can handle high power. Their low cost makes them disposable. A possibility of optical image transmission through such fibers provides additional advantages in many medical and industrial applications.

Power laser delivery fiber systems essentially consist of an appropriate constant wave, cw, or pulsed laser source as for example $CO_2$, Nd-YAG, or argon; one or more flexible optical fibers optically connected to the laser source by means of some input connector or some input optical focusing system. The fiber transmits the powerful laser radiation to its output end or handpiece.

High power lasers generally radiate a multimode beam whose traverse modes can be approximately described with the help of Gauss-Laguerre functions. For maximum delivery of laser power, it is thus desirable to have a fiber which can transmit all the generated Gauss-Laguerre laser modes. It is further known that scattering of the powerful laser beam in the fiber material and different nonlinear effects in the fiber result in destruction of the laser beam and in damage to the fiber. Generally the damage to the fiber first occurs in the vicinity of core-cladding boundaries because beam power density increases at such interfaces due to constructive interference of the incident and reflected beams and also due to defects arising from the presence of dissimilar materials in this region.

Step-index multimode fiber is not very suitable for transmission of the powerful laser beams, since the main guiding method for these fibers is the interaction of the beam with the core-cladding boundary. Step-index fibers also do not preserve well all the desired beam properties. Although power losses in such fibers may be small, image transmission is not possible with such fibers. Finally the mode structure in such fibers is not matched to the Gauss-Laguerre mode configuration of the laser beam.

Employing graded-index optical fibers ameliorates some of these problems. Traverse variation of the refractive index across the core radius provides the means for guiding the laser beam confining the beam to its longitudinal axis, due to the refractive index profile, rather than due to interaction with the core-cladding boundary. The graded-index optical fibers can provide an image transmission. Moreover, the modes in a graded-index fiber with a parabolic traverse distribution of its refractive index are described by Gauss-Laguerre functions. With effective coupling of a Gauss-Laguerre laser beam into such fibers, the laser's mode structure is preserved, providing maximum delivery of the laser energy.

Transmission of powerful laser beams through graded-index fiber with the normal exact parabolic index profile still has some disadvantages. The parabolic index profile is close to an optimum profile, having an equally spaced spectrum of the mode propagation constants. The parabolic index profile results in almost ideal focusing of all the beam rays. As a consequence of this focusing, any incident laser beam with a regular, planar or spherical, initial wavefront will exhibit a strong field localization in the fiber, especially at the first few focal regions. This leads to an enormous increase of the beam power density in these focal regions and causes different nonlinear effects, fiber damage etc.

European Patent EP 438 653 A2 offers a flexible graded-index optical fiber for transmitting the powerful laser beams with preservation of their mode structure. The fiber is optimized by combining the advantages of graded-index and step-index fibers in such a way as to provide a transmission of the Gauss-Laguerre laser beam through the fiber with preservation of its mode structure. Merely the preservation of the beam mode structure is not sufficient for effective operation of fibers in powerful laser delivery systems. In the general case of fiber excitation with an arbitrary input beam, the high power densities in the focal regions remain a problem.

Another attempted solution is a graded-index fiber with a non-optimum refractive index profile which would destroy the periodically repeating prescribed phase relations between fiber modes. The phases of different modes coming to the output end face of the fiber are equally distributed over the range of phases from 0 to $2\pi$. Interference of all the fiber modes with such distribution of phases results in a complicated speckle pattern at the output end face of the fiber. The angular extent of the output beam is greatly increased and image transmission through such a fiber is generally impossible. In these respects such fibers are not much better than step-index fibers. Generally in most laser power transmission systems, not only the absolute power transmitted, but also the achievable power density after transmission through the fiber is of key importance. Image transmission, that is focused transmission, is also required.

BRIEF SUMMARY OF THE INVENTION

It is, therefore the aim of the present invention to provide a graded-index optical fiber for high power laser delivery systems with a designed graded-index profile that provides damage free powerful laser beam propagation along with transmission of an optical image.

It is a further aim of the present invention to provide for a careful optimization of both the fiber excitation conditions and the parameters of the graded-index optical fiber, such as fiber refractive index profile, fiber length.

Briefly stated, in the present invention, a flexible fiber optic delivery system for medical and industrial applications is described that can transmit high laser power densities and optical images. A parabolic-index profile of a graded-index fiber is perturbed so as to prevent strong localization of a laser beam in the fiber's recurring focal regions. This permits transmission of high laser powers without danger of fiber damage. An additional gain in carrying capacity for the system is achieved by using a wavefront perturbation system between the laser source and the graded-index fiber. Optical image transmission is achieved by using a measured perturbation to a parabolic-index profile of the graded-index fiber with a prescribed length and a wavefront reconstruction system in combination with the wavefront perturbation system. The system has an increased laser induced damage threshold and can transmit highly focused optical images.

The above, and other objects, features and advantages of the present invention will become apparent from the following description read in conjunction with the accompanying drawings, in which like reference numbers in different drawings denote like items.

BRIEF DESCRIPTION OF PREFERRED EMBODIMENTS

Consider a graded-index fiber whose core refractive index profile is close to a parabolic index distribution, to permit guiding Gauss-Laguerre beam modes, but does not coincide exactly with an optimum index profile to prevent a strong power localization in the beam focal regions. The refractive index distribution in the core of such a graded-index fiber can be conveniently described with the help of the following polynomial index profile:

$$n^2(r) = n_o^2 - \omega^2 r^2 - 2\beta r^4 \quad 0 \leq r < a \quad (1)$$

$$n^2(a) = n_o^2 - \omega^2 a^2 - 2\beta a^4 = n_{cl}^2 \quad r \geq a \quad (2)$$

where r is the distance from the fiber axis, a is the radius of the fiber core, $n_o = n(0)$ is the refractive index at the fiber axis (at r=0), $n_{cl}$ is the refractive index of the fiber cladding, $\omega$ is the gradient parameter of the fiber characterizing the refractive index gradient in a standard parabolic-index fiber and parameter $\beta$ characterizes departure of the refractive index profile from the standard parabolic index distribution. The gradient parameter $\omega$ of a standard parabolic-index fiber can be calculated as follows:

$$\omega = \{[n_o^2 - n^2(a)]\}^{1/2}/a = [2n_o \Delta n]^{1/2}/a \quad (3)$$

where $\Delta n = n_o - n_{cl}$ is the core-cladding refractive index difference.

When parameter $\beta$ satisfies the relationship, $\beta \ll \omega^2/2a^2$, mode field configurations in a waveguide, described by equation (1), are close to the Gauss-Laguerre modes in a standard parabolic-index fiber. Such fibers can as effectively transmit Gauss-Laguerre beams generated by powerful laser sources as standard parabolic-index fibers, but without the severe increases in power density in the first few focal regions as in standard parabolic-index fibers.

It has been found that phase relations between fiber modes, which are responsible for focusing the beam inside the fiber, are more sensitive to perturbations of the index profile than mode field configurations are. A $\beta$ parameter can be chosen in such a way that a departure of the index profile from a parabolic one sufficient to prevent strong focusing of laser beam power inside the fiber is achieved without seriously affecting Gauss-Laguerre mode transmission through the fiber. More powerful laser beams are thus able to propagate without causing fiber damage.

Figure 1:
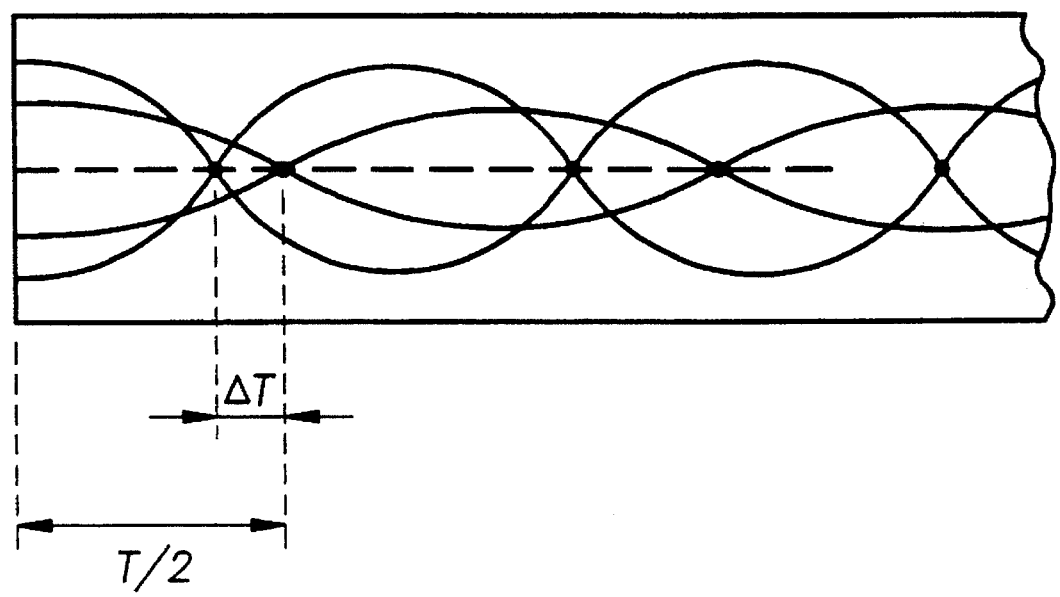
FIG. 1 shows a periodic refocusing of a beams components in a graded-index fiber of this invention.

In a standard parabolic-index fiber, beam refocusing occurs with a period equal to $T = \pi n_o/\omega$. As shown in FIG. 1, a laser beam with a planar wavefront entering a parabolic-index fiber has its paraxial beam rays, that is those propagating near the fiber's axis, focused at a distance T/2 from an input end of such fiber. As a result of the departure of the index profile from a parabolic one, a focal point for a ray propagating near the core/clad boundary, at r=a, is shifted by a distance $\Delta T$, $$\Delta T = (\pi n_o/4\omega)(3a^2\beta/\omega^2) \quad (4)$$

which is controlled by parameter $\beta$. For example to shift a focal point by $\Delta T > 0.1$ T, parameter $\beta$ should have a value given by;

$$\beta > 0.4(\omega^2/3a^2) \quad (5)$$

Figure 2:
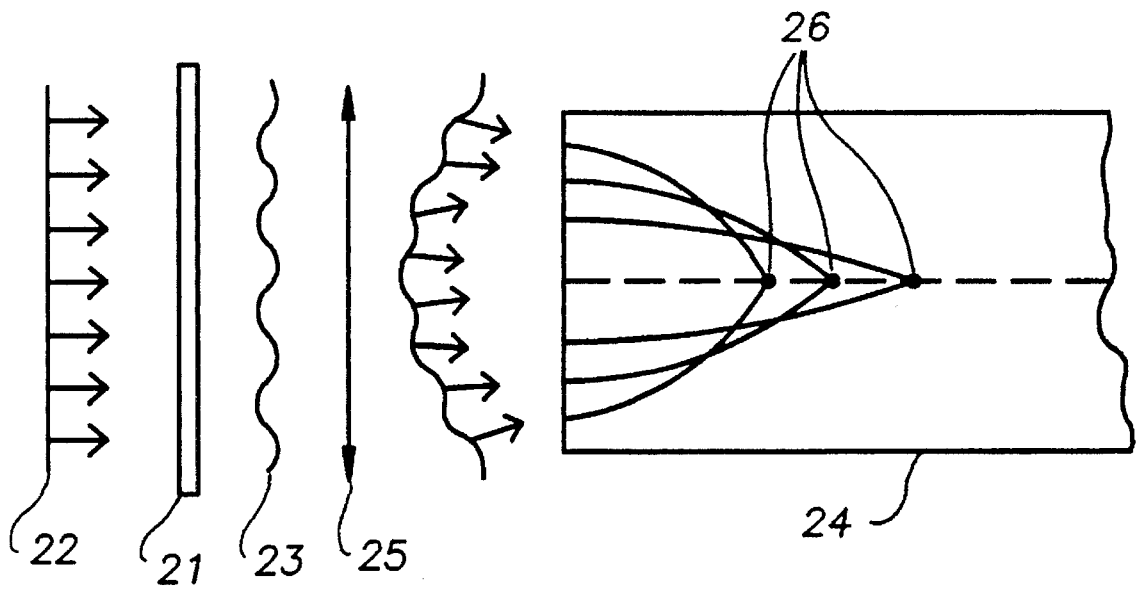
FIG. 2 shows the excitation of fiber modes with the help of wavefront perturbation system.

As shown in FIG. 2, an optical wavefront perturbation system 21 can also be used to prevent strong focusing of a laser beam inside a fiber. In such a system, a laser beam with a spherical or planar wavefront 22 transforms into a beam with a non-spherical wavefront 23. When a beam with a non-spherical wavefront 23 is coupled into a graded-index fiber 24 by means of standard optics 25 a series of focal points 26 are distributed along the fiber axis inside fiber 24 rather than a specific focal point with a strong field localization, because each section of a beam with a non-spherical wavefront 23 is different and has a different focal region.

Figure 3:
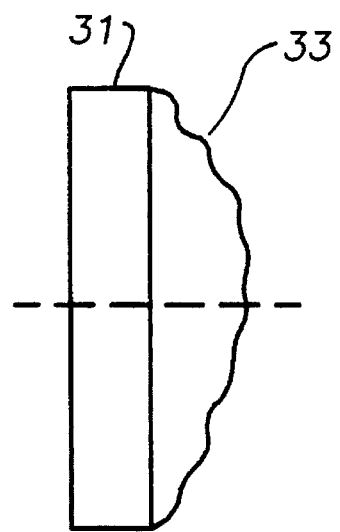
FIG. 3 shows an example of a wavefront perturbation system.

In FIG. 3, an optical wavefront perturbation system is exemplified by a lens 31 with a non-spherical surface 33 possessing strong aberrations. Alternatively a lens with a scattering surface may also function as an optical wavefront perturbation system. Additionally, well-known computer generated holograms or other wavefront correctors can be employed for perturbing a regular wavefront of a standard input laser beam.

There are many commercially important applications of high power laser delivery systems where image transmission through a fiber is also required. Parameter $\beta$, as used in equation (1), describes departure of a fiber's refractive index profile from the standard parabolic one. Its value must be large enough to prevent a strong localization of energy in beam focusing regions thus, standard image transmission resulting from multiple re-imaging of an input image along with re-focusing of rays is not feasible. It would seem that high power transmission and image transmission are somewhat exclusive goals.

It has been found that for image transmission for high power beam propagation under inspection large-scale periodic reconstruction of an initial field in a waveguide with non-optimum refractive index profile can be used. The period of such an image reconstruction is much larger than the period of beam oscillation in a waveguide. The period of image reconstruction depends on profile parameter $\beta$ and radiation wavelength $\lambda$ as follows:

$$Z=(4\pi^2 n_o)/\{\lambda(3\beta/\omega^2+\omega^2/n_o^2)\} \quad (6)$$

Figure 4:
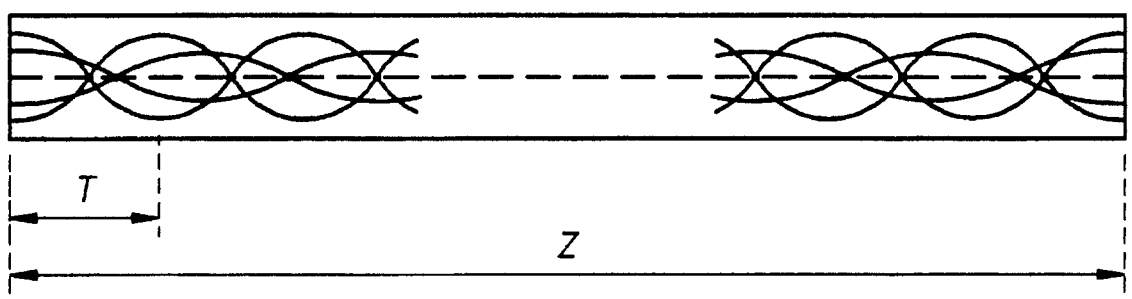
FIG. 4 illustrates a focused transmission through a graded-index fiber after a long distance.

It is not possible to explain periodic reconstruction in non-optimum refractive index profile fibers using only a simple language of geometrical optics. As shown in FIG. 4, despite a dephasing of different modes in a fiber with a non-optimum refractive index profile after propagation over a beam oscillation period T, all initial phase relations between fiber modes reconstruct themselves after a much longer propagation distance Z.

Figure 5:
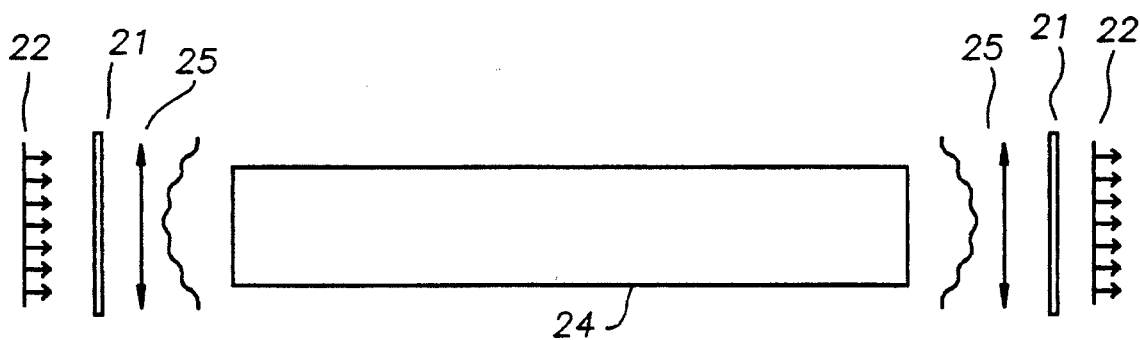
FIG. 5 shows a transmission of an image employing both wavefront perturbation and wavefront reconstitution systems.

In a preferred embodiment depicted in FIG. 5, when a wavefront perturbation system 21 is used at a fiber's input end [left side], optimum long distance image transmission through a graded index fiber of the present invention is achieved by using the same wavefront perturbation system 21 at a fiber's output end [right side] where it operates as a wavefront reconstruction system.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A flexible graded-index optical fiber for transmission of a powerful laser beam, said fiber comprising:

a core having a radius $\alpha$;

a cladding having a lower refractive index than said core;

a symmetrical axis; and a refractive index distribution correlating to the function $$n^2(r)=n_o^2-\omega^2 r^2-2\beta r^4 \quad 0\leq r<a$$

$$n^2(\alpha)=n_o^2-\omega^2\alpha^2-2\beta\alpha^4=n_{cl}^2 \quad r\geq\alpha$$

where r is the radial distance from said axis, $n_o$ is the refractive index at said axis, $n_{cl}$ is the refractive index of said cladding, $\omega$ is the gradient parameter of a standard parabolic index fiber and has the function $\omega=[2n_o(n_o-n_{cl})]^{1/2}/\alpha$, and $\beta$ is the profile parameter which represents the deviation of the refractive index profile from that of said standard parabolic index fiber, and has the relationship $\beta<<\omega^2/2\alpha^2$.

2. An optical fiber according to claim 1, wherein said fiber can also transmit images and has a length which is a multiple of the periodic image reconstruction distance Z, given by $$Z=(4\pi^2 n_o)/\{\lambda(3\beta/\omega^2+\omega^2/n_o^2)\}$$

where $\lambda$ is the wavelength of said laser beam.

3. A laser delivery system for transmission of a powerful laser beam, said system comprises at a wavefront perturbation system and a graded index optical fiber optically connected at said fiber's input end to said wavefront perturbation system.

4. A laser delivery system according to claim 3, which can also transmit images, wherein said fiber comprises:

a core having a radius $\alpha$;

a cladding having a lower refractive index than said core;

a symmetrical axis; and a refractive index distribution correlating to the function $$n^2(r)=n_o^2-\omega^2 r^2-2\beta r^4 \quad 0\leq r<\alpha$$

$$n^2(\alpha)=n_o^2-\omega^2\alpha^2-2\beta\alpha^4=n_{cl}^2 \quad r\geq\alpha$$

where r is the radial distance from said axis, $n_o$ is the refractive index at said axis, $n_{cl}$ is the refractive index of said cladding, $\omega$ is the gradient parameter of a standard parabolic index fiber and has the function $\omega=[2n_o(n_o-n_{cl})]^{1/2}/\alpha$, and $\beta$ is the profile parameter which represents the deviation of the refractive index profile from that of said standard parabolic index fiber, and has the relationship $\beta<<\omega^2/2\alpha^2$;

said fiber has a length L correlating to the function $$L=m(4\pi^2 n_o)/\{\lambda(3\beta/\omega^2+\omega^2/n_o^2)\}+i\,l$$

where $\lambda$ is the wavelength of said laser beam, m is a positive integer, and l is within the range of $$-p\times\pi n_o/\omega\leq l\leq p\times\pi n_o/\omega$$

where p is a positive integer less than 30; and said system has a wavefront reconstruction system optically connected to said fiber's output end.

5. A laser delivery system according to claim 3, wherein said wavefront perturbation system comprises a hologram.

6. A laser delivery system according to claim 4, wherein said wavefront reconstruction system comprises a hologram.

7. A laser delivery system according to claim 4, wherein said wavefront perturbation system and said wavefront reconstruction system comprise holograms.

* * * * *